(12) United States Patent
Rockwood et al.

(10) Patent No.: US 7,199,362 B2
(45) Date of Patent: Apr. 3, 2007

(54) CROSS-FLOW ION MOBILITY ANALYZER

(75) Inventors: Alan L. Rockwood, Provo, UT (US);
Edgar D. Lee, Highland, UT (US);
Nosa Agbonkonkon, Provo, UT (US);
Milton L. Lee, Pleasant Grove, UT (US)

(73) Assignee: Brigham Young University, Salt Lake City, UT (US)

( * ) Notice: Subject to any disclaimer, the term of this patent is extended or adjusted under 35 U.S.C. 154(b) by 0 days.

(21) Appl. No.: 10/821,660

(22) Filed: Apr. 9, 2004

(65) Prior Publication Data

US 2005/0006578 A1    Jan. 13, 2005

Related U.S. Application Data

(60) Provisional application No. 60/461,890, filed on Apr. 9, 2003.

(51) Int. Cl.
*H01J 49/40* (2006.01)
(52) U.S. Cl. .......................... 250/286; 250/287
(58) Field of Classification Search ................ 250/286, 250/287, 281, 282
See application file for complete search history.

(56) References Cited

U.S. PATENT DOCUMENTS

| | | | |
|---|---|---|---|
| 4,271,357 A * | 6/1981 | Bradshaw et al. .......... 250/287 |
| 6,504,149 B2 | 1/2003 | Guevremont et al. |
| 6,509,562 B1 * | 1/2003 | Yang et al. ................. 250/287 |
| 6,653,627 B2 * | 11/2003 | Guevremont et al. ....... 250/288 |
| 6,770,875 B1 * | 8/2004 | Guevremont et al. ....... 250/288 |
| 6,815,669 B1 * | 11/2004 | Miller et al. ................ 250/286 |
| 6,831,271 B1 * | 12/2004 | Guevremont et al. ....... 250/282 |
| 6,905,029 B2 | 6/2005 | Flagan |
| 2003/0136680 A1 | 7/2003 | Benner et al. |

OTHER PUBLICATIONS

"Orthogonal Extraction Ion Mobility Spectrometry", Victor V. Laiko. 2006. Journal of American Society of Mass Spectrometry, V. 17, 500-507.
"The Limits of Air Ion Mobility Resolution", H. Tammet. Institute of Environmental Physics, University of Tartu, Estonia.
"Method of Inclined Velocities in the Air Ion Mobility Analysis", H. Tammet. Institute of Environmental Physics, University of Tartu, Estonia.
"Opposed Migration Aerosol Classifier (OMAC)", Richard C. Flagan. Aerosol Science and Technology, V. 38, 890-899. 2004.

* cited by examiner

*Primary Examiner*—Kiet T. Nguyen
(74) *Attorney, Agent, or Firm*—Morriss O'Bryant Compagni

(57) ABSTRACT

A cross-flow ion mobility analyzer (CIMA) that includes a component of gas flow that opposes an electric field that is established within a channel, wherein ions are carried through the channel, wherein ions of a specific mobility are trapped by the opposing electric field and flow field within the channel and are detected when the ions reach the end of the channel, wherein a detector at the end of the channel sees a continuous stream of mobility-selected ions, and wherein different ions are selected by modifying the electric field and/or the velocity of the flow field.

66 Claims, 5 Drawing Sheets

Decay profile as registered at the detector.

CROSS-FLOW ION MOBILITY ANALYZER

CROSS REFERENCE TO RELATED APPLICATIONS

This application claims priority to provisional patent application Ser. No. 60/461,890, filed Apr. 9, 2003.

BACKGROUND OF THE INVENTION

1. Field of the Invention

This invention relates generally to separation, storage, and analysis of ions according to ion mobilities of charged particles and charged particles derived from atoms, molecules, particles, sub-atomic particles and ions. More specifically, the present invention is an ion mobility analyzer that is employed to detect a wide range of chemicals, wherein the analyzer differentiates chemical compounds based upon their ion mobilities.

2. Description of Related Art

To understand the advantages of the present invention, it is useful to examine the state of the art of mass spectrometry. Chemical analysis of charged particles and charged particles derived from ions, molecules, particles, sub-atomic particles and atoms (hereinafter to be collectively referred to as ions) can be done by separating their ionic forms according to their mass-to-charge ratios. There are various kinds of mass spectrometers. Each mass spectrometer has been found to have its own special characteristics and applications, as well as limitations. In the case of time-of-flight (TOF) mass spectrometry, the TOF mass analyzer measures the mass-to-charge (m/z) dependent time that it takes for ions of different mass-to-charge ratios to move through a flight tube from an ion source to a detector. The analysis is based on measurements of the flight time required for the ion to move along a tube of a defined length in an environment that is free of electric fields.

Time-of-flight mass spectrometry performs its analysis based on the characteristics of charge and mass of ions. In contrast, a related technique known as ion mobility mass spectrometry (IMS) is dependent upon the charge, size and shape (the cross-sectional area) of molecules to perform its analysis of ions.

IMS is a gas phase electrophoretic separation technique in which ions are separated based on their ionic mobilities as the ions drift through a buffer gas under the influence of an electric field. The analysis is based on measuring the drift time that it takes for the ion to move along a drift tube of a defined length in an applied electric field.

There are different types of IMS instruments that need to be understood in order to understand the principles of the present invention. In conventional IMS, an electric field produces a linear relationship between the drift velocity and electric field. Accordingly, reduced mobility is generally independent of the electric field. A sample is introduced into an ionization region containing an ion source. Ionized samples are then accelerated into a drift region in a drift tube, often with a buffer gas introduced from the opposite direction. Ions are separated as they drift through this buffer gas. Separation of the ions is based upon size, shape, and charge of the ions. Ions that drift through the buffer gas are registered at the detector. Conventional IMS systems generally use a low electric field and are characterized by having a low duty cycle.

In differential mobility analysis (DMA), ions are separated according to their mobilities by the application of an electric field and a flow field that are orthogonal to each other. The ions of different mobilities are dispersed in space so that only ions of a selected mobility pass through a detector slit. DMA is often used in aerosol experiments to analyze particles of a given size.

The last type of mobility analyzer is known as high-field asymmetric waveform ion mobility spectrometry, or FAIMS. In FAIMS, two concentric tubes or plates are generally used. A high electric field is applied for a short time, and then a low electric field is applied for a longer duration, with the average applied electric field being balanced. The non-linearity of the FAIMS system is generally attributed to the different cross-sectional areas of the ions that are drifting through the tube or between the plates. Accordingly, the method takes advantage of the different mobilities of ions in a high electric field as compared to a low electric field.

Another way of describing FAIMS is to say that the separation of ions is based on the nonlinear dependence of the mobility constant with respect to the electric field intensity. The change in mobility at high electric field values appears to reflect the size of the ion, its interaction with the buffer gas, and the structural rigidity of the ion. Thus, the ratio of high electric field mobility to low electric field mobility is used in the characterization of ions in FAIMS.

IMS as described by the three techniques above is a relatively fast method of ion analysis, is highly sensitive, moderately selective, and has a low limit of detection. However, IMS has generally received little attention because of its relatively poor resolution, limited linear dynamic range, and the previously mentioned low to moderate selectivity.

Accordingly, what is needed is a new form of ion mobility spectrometry that overcomes the disadvantages of the existing IMS methods. Specifically, it would be an advantage over the state of the art of IMS to be able to provide increased sensitivity, increased resolution, more accurate mobilities and specific detection.

BRIEF SUMMARY OF THE INVENTION

It is an object of the present invention to provide a method of ion mobility spectrometry that is more sensitive in particular modes of operation than existing IMS methods.

It is another object of the present invention to provide a method of ion mobility spectrometry that has increased resolution as compared to existing IMS methods.

In a preferred embodiment, the present invention is a cross-flow ion mobility analyzer (CIMA) that includes a component of gas flow that opposes an electric field that is established within a channel, wherein ions are carried through the channel, wherein ions of a specific mobility are trapped by the opposing electric field and flow field within the channel and are detected when the ions reach the end of the channel, wherein a detector at the end of the channel sees a continuous stream of mobility-selected ions, and wherein different ions are selected by modifying the electric field and/or the velocity of the flow field.

These and other objects, features, advantages and alternative aspects of the present invention will become apparent to those skilled in the art from a consideration of the following detailed description taken in combination with the accompanying drawings.

DETAILED DESCRIPTION OF THE INVENTION

Reference will now be made to the drawings in which the various elements of the present invention will be given numerical designations and in which the invention will be discussed so as to enable one skilled in the art to make and use the invention. It is to be understood that the following description is only exemplary of the principles of the present invention, and should not be viewed as narrowing the claims which follow.

The present invention is a cross-flow ion mobility analyzer (CIMA) that is capable of detecting a wide range of chemicals including pharmaceuticals, environmental pollutants, chemical and biological warfare agents, agrichemicals, and petrochemicals. An immediate need for this technology is airport screening for residues of explosives that may be present on luggage, packages, and personnel. Another useful application is characterizing sizes of lipo-proteins from blood samples. It will be understood by those skilled in the art that there are other applications for a CIMA of the present invention.

Similar to IMS, the present invention is based on the mobilities of ions created from target analytes. However, the new cross-flow ion mobility analyzer technology uses a modified principle of operation to differentiate compounds based on their ion mobilities, and promises enhanced sensitivity and greatly enhanced resolution over all previous implementations of IMS, including conventional, differential, and FAIMS. The present invention results in more accurate and specific detection of chemicals.

Figure 1:
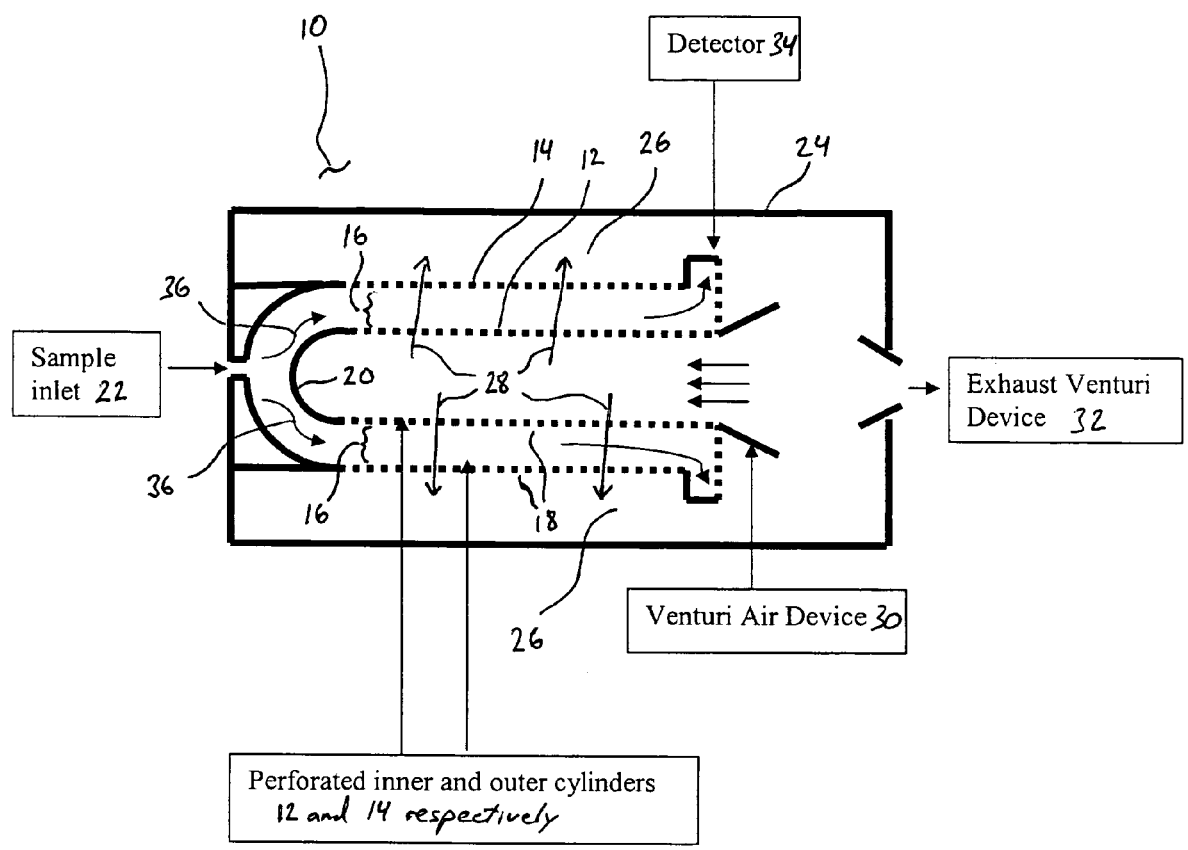
FIG. 1 is a schematic drawing of the first embodiment of a cross-flow ion mobility spectrometer comprised of concentric cylinders as electrodes of the system.

The present invention is illustrated in a first embodiment in FIG. 1. FIG. 1 is a cross-sectional schematic diagram of the CIMA device 10. The CIMA device includes a drift region (i.e. a cross-flow region) that is formed by the gap or space 16 between two concentric metal cylinders 12, 14 that are approximately 6 inches long. It should be understood that this first embodiment that uses cylinders is for illustration purposes only.

Alternative embodiments of the present invention include replacing the two concentric cylinders 12, 14 with electrodes that can create an electric field between them. For example, concentric spheres, a series of stacked electrodes, substantially parallel plates, and non-parallel plates can also be used. One of the distinct advantages of the first embodiment of concentric cylinders 12, 14 is to minimize edge effects on laminar flow and electric fields.

Returning to the first embodiment, the inner cylinder 12 has a diameter of 2 inches and the outer cylinder 14 has a diameter of 4 inches, thereby leaving a one inch gap 16 between the cylinders 12, 14. The middle 4-inch lengths of both cylinders 12, 14 include holes 18 (approximately 10,000 each) that are approximately 0.0128 inches in diameter. The thickness of the cylinders 12, 14 is approximately 0.25 inches. A front end of the cylinders 12, 14 include a hemispherical end cap 20. The end cap 20 serves at least the function of delivering ions to the gas cross-flow region 16 between the cylinders 12, 14. An inlet aperture 22 through the end cap 20 functions as an inlet for the ions that are to be separated by their mobilities in the gas cross-flow region 16.

The inlet aperture 22 in the end cap 20 will typically be coupled to some ion source (not shown). It should be understood that any appropriate atmospheric ionization techniques can be used to create ions for delivery to the CIMA device 10. The following is a list of some commonly used ionization techniques: electron impact, chemical ionization, fast ion or atom bombardment, field desorption, laser desorption, plasma desorption, thermospray, electrospray, photoionization, inductively coupled plasma, and atmospheric pressure ionization. This list should be considered as representative only, and is not intended to exclude other appropriate ionization systems that may also be used with the CIMA device 10 of the present invention.

In one alternative embodiment, an ionization chamber is disposed directly adjacent to the aperture inlet 22 where samples can be ionized immediately before being drawn into the cylinders 12, 14.

The CIMA device 10 is housed in an enclosure or housing 24 that is sealed to thereby maintain the appropriate pressure and constant gas flow that is needed for operation of the present invention which will now be explained.

In operation of the first embodiment, the housing 24 is first purged of air and bathed in nitrogen gas. Both the inner and outer cylinders 12, 14 are coupled to at least two voltage sources (if ground is considered a voltage source) (not shown) so that both cylinders 12, 14 function as electrodes. The cylinders 12, 14 are set at different potentials to thereby generate a potential between the first cylinder 12 and the second cylinder 14.

In the example configuration shown in FIG. 1, the desired range for electrical potentials will generally vary from hundreds up to thousands of volts. However, it should be remembered that for whatever size of electric field that is established between the cylinders 12, 14, there will be an opposing gas flow that must be sufficiently strong enough to create a balancing effect. Nevertheless, it is possible to increase or decrease the electrical potential and the opposing fluid flow depending upon the desired performance of the present invention.

The significance of the fact that the present invention operates using electric potentials in the hundreds and perhaps thousands of volts is worth noting. One implication of this fact is that the present invention operates with voltages that are much easier to operate with than the tens of thousands of volts that are part of at least conventional and FAIMS IMS systems.

Along with the electric field that is established in the cross-flow region 16 between the cylinders 12, 14, a critical aspect of the present invention is the creation of a cross-flow of gas that opposes the electric field. A velocity of the gas cross-flow is therefore set to any appropriate value as known to those skilled in the art. The gas cross-flow is shown in FIG. 1 as being created by a flow of a gas into the first cylinder 12 that is directed outwards through the holes 18 into the cross-flow region 16, and then through the holes 18 in the second cylinder 14 into a space 26 in the housing 24.

This gas cross-flow is represented by lines 28. FIG. 1 indicates that a venturi air device 30 directs the gas cross-flow into the first cylinder 12. An exhaust aperture 32 is also shown in the housing 24.

Some aspects of the present invention that can be explained at this point include the fact that the housing 24 can operate at normal atmospheric pressure, at an elevated pressure, or at a reduced pressure, depending upon the desired performance of the CIMA device 10. Furthermore, it is possible to operate certain regions of the CIMA device 10 at one pressure, and a different region at a different pressure. For example, the gas cross-flow region 16 may be at a first pressure, and the ions may be drawn into a detection area that operates at a different second pressure.

Another aspect of the present invention that bears explanation is that it is recognized that the gas cross-flow velocity decreases as the gas moves from the inner cylinder 12 to the outer cylinder 14. What is not immediately apparent is that the strength of the electric field changes in the same proportion as the gas cross-flow velocity. Accordingly, a balanced condition is maintained in the gas cross-flow region 16 between the cylinders 12, 14 regardless of the position of the ions of selected mobilities.

Related to this concept of having a balanced condition is the concept of a fastscan. The balance condition needs to remain the same as an ion travels through the CIMA instrument 10. However, as the CIMA instrument 10 is used to perform a scan, an ion that is in balance when it is at a beginning point of the gas cross-flow region 16 will be out of balance when it arrives at an exit point because the electric field changes. For example, when scanning from a low voltage to a high voltage, the voltage is too high by the time the ion reaches the exit point, so it is out of balance and is ejected.

A solution to this problem in the present invention is to arrange electrodes (the cylinders 12, 14) so that at any given instant, the electric field for an ion near the exit point is less than for an ion near the entry point, assuming that it is possible to perform a scan from low to high voltage. It should be apparent that it is possible to simply reverse the process if scanning is in the opposite direction (i.e. from a high voltage to a low voltage). One method of performing this action is to break the electrodes into electrically isolated sections and apply voltages separately to each section. Another way is to simply make the electrodes non-parallel. The end result of either scheme is to create a desired voltage gradient to compensate for creating an unbalanced situation.

Another solution is to make the gas cross-flow velocity lower at the exit point than at the entry point. This assumes that the system is being used to scan from low to high voltage. Again it should be apparent that it is possible to simply reverse the process if scanning is in the opposite direction (i.e. from a high voltage to a low voltage).

In a final alternative, it is possible to combine the methods of creating a desired voltage gradient with the change in gas cross-flow velocity.

With the operation of the CIMA device 10 as described above, wherein an electric field is generated between two cylinders 12, 14, and an opposing gas cross-flow is created in the same region, the present invention is capable of operating in a trapping mode. In other words, ions will be trapped within the gas cross-flow region 16 if there is no force to move them out. This trapping mode may be useful for gathering ions that can then be delivered from the gas cross-flow region 16, for example, in a pulsed mode.

Nevertheless, in an alternative embodiment, the present invention also includes the creation of an axial gas flow which is represented by lines 36. The axial gas flow also operates within the gas cross-flow region 16, but operates independently of the gas cross-flow, and flows along a long axis of the cylinders 12, 14, substantially perpendicular to the gas cross-flow. However, the net gas flow is the combination of the axial gas flow and the gas cross-flow.

It is observed that the axial gas flow may affect the resolution of the CIMA device 10. The slower the axial gas flow, the higher the predicted resolution.

In essence, when ions are injected into the system at the sample inlet aperture 22, the axial gas flow draws the ions into and then carries them through the cross-flow region 16 where the electric field applied in one direction and gas cross-flow in an opposing direction is used to separate the ions based on their mobilities. It should be mentioned that while a vacuum pump may be used to draw the ions into the gas cross-flow region 16, other systems can be used to cause this effect. The gas cross-flow assists in separating and suspending ions in space in the gas cross-flow region 16.

When the CIMA device 10 is functioning as a detection device, a detector 34 is generally going to be disposed at the end of the gas cross-flow region 16. The detector 34 is maintained at a zero potential so that ions leaving the high electric field of the gas cross-flow region 16 will enter a controlled-voltage zone, and collapse without interference into the detector where they are registered.

It is noted that the first embodiment does not include any sort of slit in front of the detector 34. However, it is observed that an aperture could be disposed between the gas cross-flow region 16 and the detector 34 that could lead to a different detector or detection system. The aperture can be comprised of a slit, a plurality of slits, holes, etc.

Regarding a gas that is used in the CIMA device 10, it was mentioned that nitrogen is used as the gas cross-flow. Nitrogen was selected because of its inert nature. Other inert gases can be used. However, in another aspect of the present invention, modifying gases could also be selected. A modifying gas is a gas in which the transport properties of ions are different from those referred to previously.

Another aspect of the present invention that bears discussion is the affect of temperature on performance. It may be that ion mobilities may be affected by the temperature at which the ions are being separated. Accordingly, ion mobilities may be increased or decreased depending upon whether or not temperature of the ions is decreased or increased.

Figure 2:
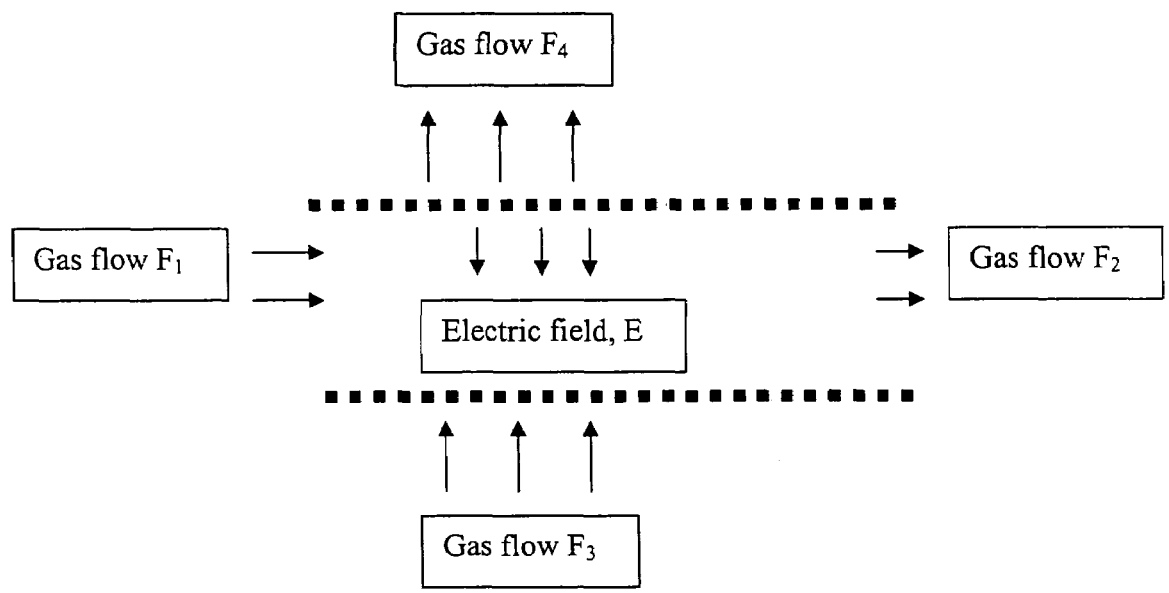
FIG. 2 is an illustration of fluid flow in relation to the electrodes and the electric field that is disposed between them.

In the present invention, it was previously mentioned that it is possible to suspend ions of a given mobility in the gas cross-flow region 16. The amount of time that the ions can remain suspended is limited by diffusion to walls of the cylinders 12, 14. It is noted that the term "diffusion" as used here is meant to refer to turbulent and dispersive diffusion as understood by those skilled in the art. FIG. 2 is provided as an illustration of how this is achieved. It is noted that this is in the context of also having a changeable electric field or gas cross-flow.

In the CIMA device 10 illustrated in the first embodiment, FIG. 2 illustrates that the effort is directed to making $F_3$ equal $F_4$ to thereby obtain suspension of the ions in the gas cross-flow region 16. However, diffusion of ions toward the walls of the cylinder 12, 14 can be limited or reduced by some type of focusing method.

Referring to FIG. 2, mass conservation requires that the total net flow of the flows F1 through F4 into or out of the device is zero. Thus, any three of the flows may be inde pendently controlled. In this process, the gas flow F1 must be into the CIMA device 10 or the ions will be prevented from entering the CIMA device 10.

There are at least two ways in which focusing can be achieved. The first focusing method for the present invention is to make $F_3$ greater than $F_4$. This action pushes ions toward the opposite cylinder wall. To suspend the ion in the gap (cross-flow region) requires that the electric field be slightly increased. This combination produces a focusing effect. The point of focus can be moved by adjusting the electric field or the gas cross-flow. Ions of a given mobility range (a passband) are focused within the gap, and ions outside of the range are pushed to one wall or the other, and will not reach the detector 24. Each mobility value that is focused within the gas cross-flow region 16 is focused on a different position within the gap.

The second focusing method for the present invention is achieved by superimposing a small parabolic potential over the electric field. The parabolic potential is a perturbation of the electric field opposing the gas cross-flow. Adding this electric field is a close analogy to modifying the flow field in the previous paragraph. However, it should be understood that while focusing decreases the resolution of the CIMA device 10, it increases transmission efficiency.

The following material explains the principles upon which the present invention is based, as well as some simulation results that confirm operation as desired. In the new CIMA device 10 of the present invention, ions are separated in a region where two opposing forces act on the ion: an electric field in one direction and a buffer gas flow (gas cross-flow) in the opposite direction. Ions are suspended and separated in the center of an annular region (gas cross-flow region 16).

Unlike IMS techniques where ions drift from one end of a cylinder to the other and are separated, separation occurs in the CIMA device 10 of the present invention as ions that are suspended from each other between the cylinder walls of the annular region (separation in one direction) and move from injection point to detector (separation in second direction, i.e. "axial direction") by the weak axial gas flow. Alternatively, a weak axial electric field can be superimposed on the electric field. However, it has been determined that it is easier to generate the axial gas flow rather than the weak axial field.

The following equation is representation of the distribution of the ions across the gas cross-flow region 16. This first equation is therefore simply a representation of a calculation that can be performed that represents a simplified model of one aspect of the CIMA device 10. The simplified model is represented by the equation $$\frac{\partial C}{\partial t} = D \frac{\partial^2 C}{\partial x^2} - V \frac{\partial C}{\partial x},$$

where D=diffusion coefficient, C=concentration of analyte, V=flow velocity which is a sum of $v_g$ and $v_d$, $v_g$=velocity of gas (gas cross-flow velocity), and $v_d$=velocity of drift (caused by electric field). It should be understood that $v_d$ is a function of the mobility and electric field (i.e. $v_d$=KE, where K is the mobility constant and E is electric field strength). D is related to the mobility by the equation $$K = \frac{eD}{kT},$$

(assuming normal or dispersive diffusion, and not turbulent diffusion) where K=the mobility constant, e=ionic charge, k=Boltzmann constant, T=gas temperature, and D=diffusion coefficient.

Using appropriate units (K in cm$^2$ V$^{-1}$s$^{-1}$, D in cm$^2$ s$^{-1}$, and T in Kelvin), $$K = 1.1605 \times 10^4 \frac{D}{T}.$$

Solving the differential equation gives two trial solutions, a "cosine" and "sine" solutions, which are $$F(x,t) = \exp\left(\left(-\frac{V^2}{2D} - \frac{4D\pi^2}{L^2}(n-0.5)^2\right)t\right)\exp\left(\frac{V}{2D}x\right)\cos\left(2\pi\left(\frac{n-0.5}{L}\right)x\right) \text{ and}$$

$$G(x,t) = \exp\left(\left(-\frac{V^2}{2D} - \frac{4D\pi^2}{L^2}n^2\right)t\right)\exp\left(\frac{V}{2D}x\right)\sin\left(2\pi\frac{n}{L}x\right),$$

where n=the number of half waveforms between the boundary. At boundary conditions, the concentration becomes zero as ions are lost when they collide at the walls of the container. Within the space between the walls (i.e. the gas cross-flow region 16) the total ion concentration is expressed as $$C(x,t) = \sum_{n=1}^{\infty} A_n F_n(x,t) + B_n G_n(x,t).$$

How much of the initial concentration makes it to the detector 34 is a measure of the transmission efficiency of this method. The resolution is how well sample ions are separated between the walls and along the path (gas cross-flow region 16) between cylinders 12, 14 to the detector 34 as compared to ions of slightly different mobilities.

The CIMA device 10 of the present invention can be compared to FAIMS in which the gas cross-flow is likened to the asymmetric AC voltage and changing static electric field compared to compensation voltage in FAIMS. In a theoretical study, a 1,000 V/cm potential was applied to a 10 cm tube to achieve a resolution of 1400. The suspending effect of the opposing gas flow is what actually makes CIMA a more selective and resolving method.

Preliminary work was done by developing a mathematical model for CIMA, and then performing simulations for the proof of principle of the CIMA concept. Several injection profiles were simulated using a beta distribution function. This beta distribution function is given as $$C(x,t=0) = \left(\frac{1}{2} + \frac{x}{L}\right)^{\alpha-1}\left(\frac{1}{2} - \frac{x}{L}\right)^{\beta-1}\frac{1}{L}\frac{\gamma(\alpha+\beta)}{\gamma(\alpha)\gamma(\beta)},$$

where α>0, β>0. γ(α+β) is the gamma function defined as $$\gamma(\alpha) = \int_0^\infty x^{\alpha-1} e^{-x} dx.$$

Figure 3:
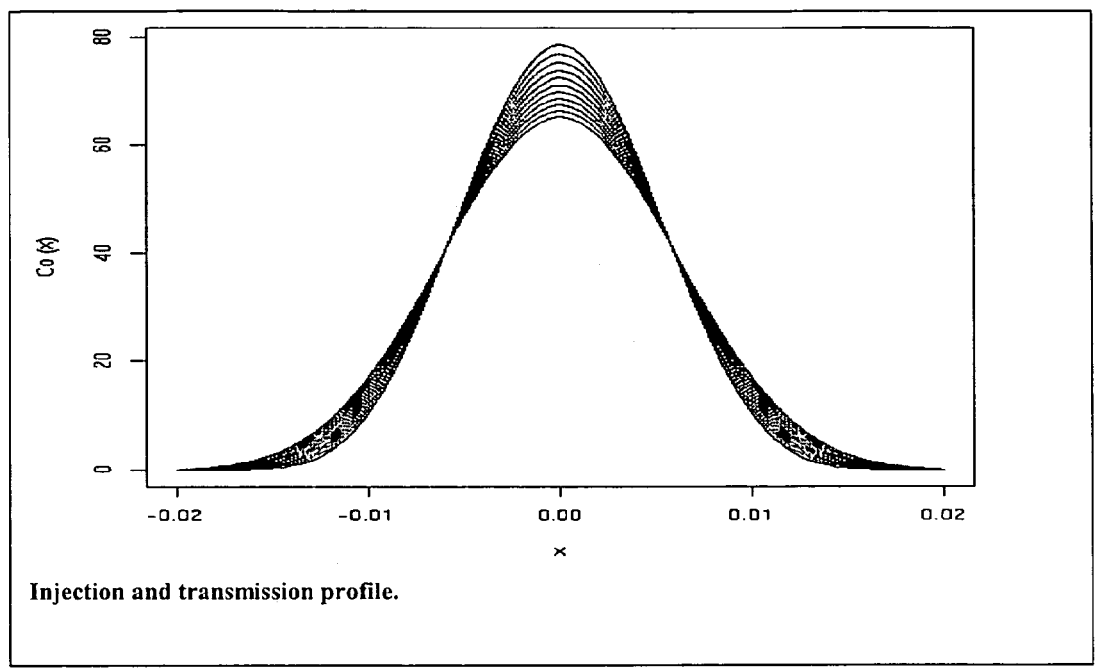
FIG. 3 is a graph describing an injection and transmission profile from the cross-flow ion mobility system.

For example, consider the following injection and transmission profiles in FIG. 3, depending on the alpha and beta values chosen. At t=0, when a sample is injected into a CIMA device, it is possible to model the concentration to fit into any of the profiles in FIG. 1, and $C(x,t=0)=\Sigma A_n F_n(x, t=0)+\Sigma B_n G_n(x,t=0)$. The equation above is solved by first finding all values of $A_n$ and $B_n$, which when summed together reproduce the original profile. From the equation above, the solutions for $A_n$ and $B_n$ are given as follows:

$$A_k = \frac{\int_{-L/2}^{L/2} C(x, t=0) \exp\left(-\frac{V}{2D}x\right) \cos\left(2\pi\left(\frac{k-0.5}{L}\right)x\right)}{\int_{-L/2}^{L/2} \cos^2\left(2\pi\left(\frac{k-0.5}{L}\right)x\right)}, \text{ and}$$

$$B_k = \frac{\int_{-L/2}^{L/2} C(x, t=0) \exp\left(-\frac{V}{2D}x\right) \sin\left(2\pi\frac{k}{L}x\right)}{\int_{-L/2}^{L/2} \sin^2\left(2\pi\frac{k}{L}x\right)} \text{ respectively.}$$

Where k takes values from 1 to infinity.

A computer program was used for statistical modeling to perform the simulation. The injection profile was simulated to determine an optimal entrance slit, then a decay profile that reproduces the concentration decay as the analyte moves from the injection port to the detector, and finally the detector spectral output. In an actual simulation, the series is truncated to something less than infinity for practical purposes.

The following parameters were used for the simulation: a drift cylinder of 10 cm, a plate gap of 3 cm, flight time from injection to detector of 1 second, an axial length of 10 cm, a gas cross-flow velocity of 10 m/s and a voltage of 10 kV. The following compounds with their $K_0$ were used: methylamine, 2.65; ethylamine, 2.36; formamide, 2.45; dimethylamine, 2.46; and isopropylamine, 2.20; in reduced mobility units of $cm^2/V/s$.

In the simulation, an equal amount of the five samples was injected into the system. These plots show some very interesting and unexpected results. The first figure shows transmission of analytes within opposing fields, namely; the gas cross-flow and an opposing electric field. FIG. 3 shows how most of the sample distribution is centered in the gas cross-flow region 16.

Figure 4:
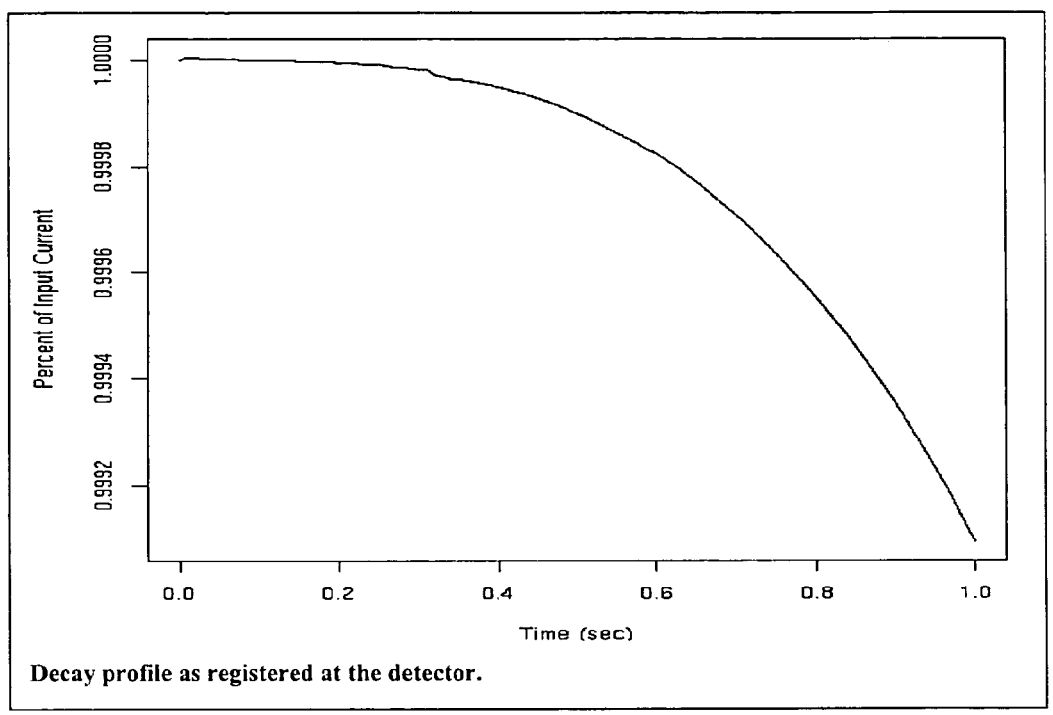
FIG. 4 is a graph describing a decay profile from the cross-flow ion mobility system.

FIG. 4 shows a typical decay profile in one second. It is interesting to note that there is a transmission efficiency of about 99%. This transmission efficiency shows that most of the injected sample is not lost to the wall, but that it reaches the detector.

Figure 5:
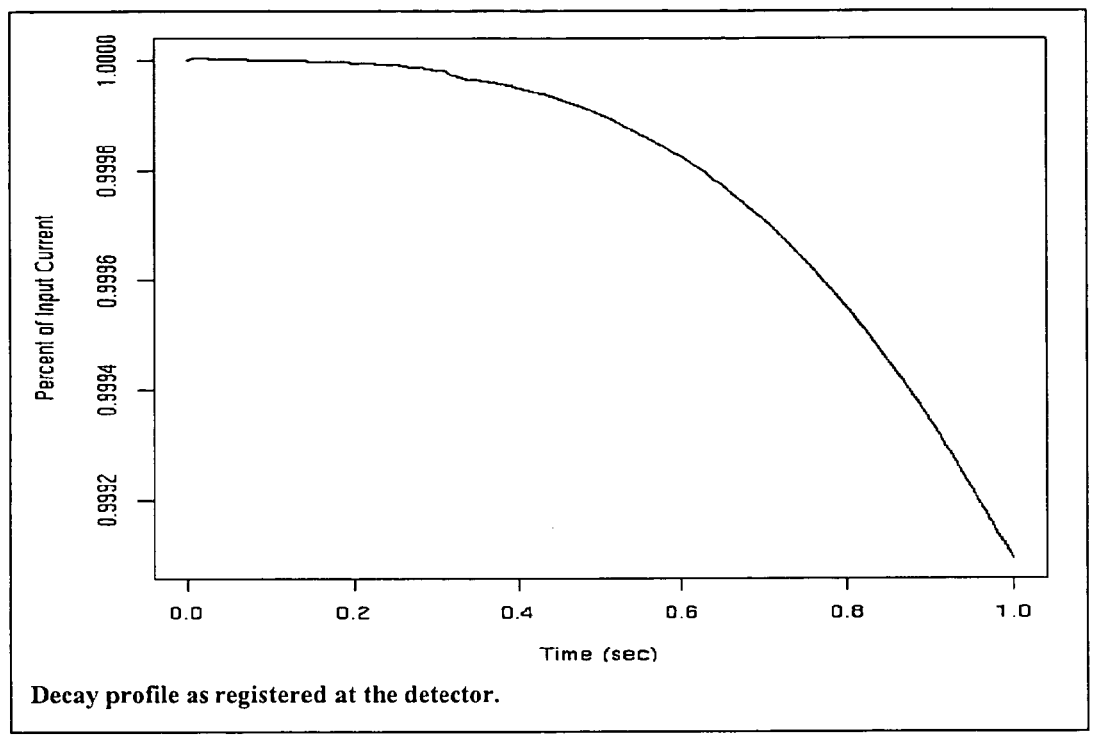
FIG. 5 is a graph describing an ion spectrum from the cross-flow ion mobility system.

FIG. 5 shows the detector output in a scanned electric field (i.e. scanned mobility spectrum). Calculation of resolution gives a value of 1400 full-width at half peak maximum.

The following generalizations are drawn from the simulation results: a resolution greater than the resolution value predicted or achieved by traditional IMS methods. Enhanced selectivity is possible as the simulation shows that compounds with reduced mobility difference of 0.01 unit can be separated. The transmission efficiency shows that CIMA will improve detection limits when operated in a selected mobility operating mode as compared to the levels currently achieved by the traditional IMS methods, as less than 1% of the initial sample is lost.

In an alternative aspect of the present invention, it should be understood that although the present invention is a gas phase device, the present invention can also operate with liquids. For example, in comparison to capillary electrophoresis, there is virtually no electro-osmotic flow. Furthermore, the present invention is a continuous rather than a pulsed system that is useful for preparative as well as analytical separations.

Regarding detectors, the present invention can use detectors based on Faraday detection, electron multiplier, multichannel plate, charge-coupled detectors, an array detector, or any other detection method including mass spectrometry or IMS (with or without collision cells). The analyzer and detector can separate and detect either positive or negative ions separately, or both positive and negative ions at the same time using parallel cross-flow channels.

The present invention can be operated so as to monitor a single ion, or several selected ions at the same time, scanned through a predetermined mobility range, or with an array detector to monitor all ions simultaneously separated in space.

An additional aspect of the present invention includes the ability to provide additional selectivity by applying an asymmetric electric waveform between the electrodes of the CIMA device 10, similar to what is practiced in FAIMS. However, no DC field is needed because the gas flow takes the place of the DC field. In addition, the present invention can be configured such that one half of the CIMA device 10 operates with a direct DC potential between the electrodes, and the other half operates with a high field asymmetric waveform potential between the electrodes. Furthermore, the asymmetric waveform could also be superimposed on a DC potential.

It is to be understood that the above-described arrangements are only illustrative of the application of the principles of the present invention. Numerous modifications and alternative arrangements may be devised by those skilled in the art without departing from the spirit and scope of the present invention. The appended claims are intended to cover such modifications and arrangements.

What is claimed is:

1. A cross-flow ion mobility system for separating ions according to ion mobilities of charged particles and charged particles derived from atoms, molecules, particles, subatomic particles and ions, said system comprised of:
    at least two electrodes disposed so as to create an electric field therebetween;
    a first fluid flow that is substantially in opposition to the electric field; and
    wherein the electric field and the first fluid flow are substantially perpendicular to a direction of travel of atoms, molecules, particles, sub-atomic particles and ions through the system to a detector.

2. The cross-flow ion mobility system as defined in claim 1 wherein the first fluid flow is comprised of a gas.

3. The cross-flow ion mobility system as defined in claim 2 wherein the gas of the first fluid flow is selected from the group of gases comprised of inert gases.

4. The cross-flow ion mobility system as defined in claim 2 wherein the gas of the first fluid flow is selected from the group of gases comprised of modifying gases, wherein, a modifying gas is a gas in which the transport properties of ions have been changed.

5. The cross-flow ion mobility system as defined in claim 1 wherein the first fluid flow is comprised of a liquid.

6. The cross-flow ion mobility system as defined in claim 1 wherein the at least two electrodes are at least partially permeable to the first fluid flow.

7. The cross-flow ion mobility system as defined in claim 6 wherein the at least two electrodes are selected from the group of electrodes comprised of at least two concentric cylinders, at least two concentric spheres, a plurality of stacked plates, at least two substantially parallel plates, and at least two substantially non-parallel plates.

8. The cross-flow ion mobility system as defined in claim 7 wherein the at least two concentric cylinders are further comprised of a first cylinder and a second cylinder, wherein a gap between the first cylinder and the second cylinder defines a gas cross-flow region.

9. The cross-flow ion mobility system as defined in claim 8 wherein the first cylinder and the second cylinder include a plurality of apertures therethrough, wherein the plurality of apertures enable a gas cross-flow to pass from inside the first cylinder, through the gas cross-flow region, and out through the second cylinder.

10. The cross-flow ion mobility system as defined in claim 9 wherein the system is further comprised of an end cap that is coupled to a first end of the first cylinder and the second cylinder, wherein the end cap creates a seal at the first end that functions as an entry for ions to be delivered to the gas cross-flow region.

11. The cross-flow ion mobility system as defined in claim 10 wherein the end cap is further comprised of an inlet aperture disposed in an end thereof, wherein the inlet aperture receives ions to be delivered to the gas cross-flow region.

12. The cross-flow ion mobility system as defined in claim 11 wherein the system is further comprised of an ion source, wherein the ion source is disposed adjacent to the inlet aperture for delivery of ions thereto.

13. The cross-flow ion mobility system as defined in claim 12 wherein the housing further comprises an air tight seal such that the system can operate at an elevated pressure, at atmospheric pressure, or at reduced pressure.

14. The cross-flow ion mobility system as defined in claim 13 wherein the housing further comprises an insulated device, wherein the system can operate at an elevated temperature, at room temperature, and at a reduced temperature.

15. The cross-flow ion mobility system as defined in claim 14 wherein the system is further comprised of means for increasing and decreasing a velocity of the first fluid flow.

16. The cross-flow ion mobility system as defined in claim 15 wherein the system is further comprised of a means for increasing and decreasing a velocity of the second fluid flow.

17. The cross-flow ion mobility system as defined in claim 16 wherein the system is further comprised of a means for increasing and decreasing an electric potential on the at least two electrodes, whereby the electric field can be increased and decreased.

18. The cross-flow ion mobility system as defined in claim 9 wherein the system is further comprised of a detector.

19. The cross-flow ion mobility system as defined in claim 18 wherein the detector is disposed at a second end of the first cylinder and the second cylinder, opposite the end cap.

20. The cross-flow ion mobility system as defined in claim 19 wherein the detector is selected from the group of detectors comprised of a Faraday detector, electron multiplier, multi-channel plate, a mass spectrometer, another ion mobility analyzer, an array detector and a charge-coupled detector.

21. The cross-flow ion mobility system as defined in claim 20 wherein the system further comprises a housing, wherein the first cylinder and the second cylinder are disposed within the housing to thereby control fluid flow therein.

22. The cross-flow ion mobility system as defined in claim 21 wherein the first fluid flow is through the gas cross-flow region.

23. The cross-flow ion mobility system as defined in claim 22 wherein the system is further comprised of a second fluid flow, wherein the second fluid flow is substantially perpendicular to the first fluid flow, and wherein the second fluid flow is generally parallel to a long axis of the first cylinder and the second cylinder, and wherein the second fluid flow defines a direction of travel of atoms, molecules, particles, sub-atomic particles and ions through the system to a detector.

24. The cross-flow ion mobility system as defined in claim 23 wherein the system further comprises a net fluid flow, wherein the net fluid flow is the combination of the first fluid flow and the second fluid flow.

25. The cross-flow ion mobility system as defined in claim 1 wherein the system is further comprised of a voltage source, wherein the voltage source is coupled to the at least two electrodes to thereby enable creation of the electric field.

26. The cross-flow ion mobility system as defined in claim 1 wherein the system is further comprised of means for analyzing ions, wherein the means for analyzing includes the ability to enable the system to only pass at least one ion of a known mobility.

27. The cross-flow ion mobility system as defined in claim 1 wherein the system is further comprised of means for measuring ions, wherein the means for measuring includes the ability to scan through a range of ion mobilities, select a particular ion mobility peak, and relate the selected ion mobility peak to gas cross-flow velocity and the opposing electric field.

28. The cross-flow ion mobility system as defined in claim 1 wherein the system further comprises means for generating a high electric field asymmetric waveform.

29. The cross-flow ion mobility system as defined in claim 1 wherein the system also performs chemical and physical analysis, said system further comprising:
 a means for introducing ions from a sample to the cross-flow ion mobility system;
 a means for detecting the ions from the sample;
 a means for obtaining a measure of selected ion mobilities from the sample; and
 a means for relating the measure of selected ion mobilities from the sample to a chemical identity or at least one physical property.

30. A method for separating ions according to ion mobilities of charged particles and charged particles derived from atoms, molecules, particles, sub-atomic particles and ions, said method comprised of:
 1) providing a cross-flow ion mobility system comprised of at least two electrodes disposed so as to create an electric field therebetween, and a first fluid flow that is substantially in opposition to the electric field, wherein the electric field and the first fluid flow are substantially perpendicular to a direction of travel of atoms, molecules, particles, sub-atomic particles and ions through the system; and 2) separating ions based upon charge, size and cross-sectional area of the ions.

31. The method as defined in claim 30 wherein the method further comprises the step of creating the first fluid flow from a gas.

32. The method as defined in claim 30 wherein the method further comprises the step of creating the first fluid flow from a liquid.

33. The method as defined in claim 30 wherein the method further comprises the step of making the at least two electrode at least partially permeable to the first fluid flow to thereby enable the creation of a fluid cross-flow in the system.

34. The method as defined in claim 33 wherein the method further comprises the step of selecting the at least two electrodes from the group of electrodes comprised of at least two concentric cylinders, at least two concentric spheres, a plurality of stacked plates, at least two substantially parallel plates, and at least two substantially non-parallel plates.

35. The method as defined in claim 34 wherein the method further comprises the steps of:
   1) selecting a first and a second concentric cylinders as the at least two electrodes; and
   2) defining a gap between the first cylinder and the second cylinder as a gas cross-flow region wherein the ions are separate according to ion mobilities.

36. The method as defined in claim 35 wherein the method further comprises the steps of creating a plurality of apertures through the first cylinder and the second cylinder to thereby enable a gas cross-flow to pass from inside the first cylinder, through the gas cross-flow region, and out through the plurality of apertures in the second cylinder.

37. The method as defined in claim 36 wherein the method further comprises the step of coupling an end cap to a first end of the first cylinder and the second cylinder, wherein the end cap creates a seal at the first end that functions as an entry for ions to be delivered to the gas cross-flow region.

38. The method as defined in claim 37 wherein the method further comprises the step of disposing an inlet aperture in an end thereof, wherein the inlet aperture receives ions to be delivered to the gas cross-flow region.

39. The method as defined in claim 38 wherein the method further comprises the step of providing an ion detector.

40. The method as defined in claim 39 wherein the method further comprises the step of disposing the detector at a second end of the first cylinder and the second cylinder, opposite the end cap.

41. The method as defined in claim 40 wherein the method further comprises the step of selecting the detector from the group of detectors comprised of a Faraday detector, electron multiplier, multi-channel plate, a mass spectrometer, an ion mobility analyzer, an array detector and a charge-coupled detector.

42. The method as defined in claim 41 wherein the method further comprises the step of disposing a housing around the first cylinder and the second cylinder to thereby control fluid flow therein.

43. The method as defined in claim 42 wherein the method further comprises the step of directing the first fluid flow through the gas cross-flow region.

44. The method as defined in claim 43 wherein the method further comprises the step of providing a second fluid flow that is substantially perpendicular to the first fluid flow, and wherein the second fluid flow is generally parallel to a long axis of the first cylinder and the second cylinder, and wherein the electric field and the first fluid flow are substantially perpendicular to a direction of travel of atoms, molecules, particles, sub-atomic particles and ions through the cross-flow ion mobility system.

45. The method as defined in claim 44 wherein the method further comprises the step of providing an ion source, wherein the ion source is disposed adjacent to the inlet aperture for delivery of ions thereto.

46. The method as defined in claim 45 wherein the method further comprises the step of making an air tight seal for the housing such that the system can operate at an elevated pressure, at atmospheric pressure, or at reduced pressure.

47. The method as defined in claim 46 wherein the method further comprises the step of insulating the housing such that the system can operate at an elevated temperature, at room temperature, and at a reduced temperature to thereby alter ion mobilities.

48. The method as defined in claim 47 wherein the method further comprises the step of providing means for increasing and decreasing a velocity of the first fluid flow to thereby alter ion mobilities.

49. The method as defined in claim 48 wherein the method further comprises the step of providing means for increasing and decreasing a velocity of the second fluid flow.

50. The method as defined in claim 49 wherein the method further comprises the step of providing means for increasing and decreasing an electric potential on the at least two electrodes, whereby the electric field can be increased and decreased to thereby alter ion mobilities.

51. The method as defined in claim 50 wherein the method further comprises the step of selecting the first fluid flow from the group of gases comprised of inert gases.

52. The method as defined in claim 51 wherein the method further comprises the step of selecting the first fluid flow from the group of gases comprised of modifying gases, wherein, a modifying gas is a gas in which the transport properties of ions have been changed.

53. The method as defined in claim 52 wherein the method further comprises the step of providing means for analyzing ions, wherein the means for analyzing includes the ability to enable the system to only pass at least one ion of a known mobility.

54. The method as defined in claim 53 wherein the method further comprises the steps of:
   1) providing means for measuring ions;
   2) scanning through a range of ion mobilities;
   3) selecting a particular ion mobility peak; and
   4) relating the selected ion mobility peak to gas cross-flow velocity and the opposing electric field.

55. The method as defined in claim 30 wherein the method further comprises the step of providing a voltage source, wherein the voltage source is coupled to the at least two electrodes to thereby enable creation of the electric field.

56. The method as defined in claim 30 wherein the method further comprises the step of performing chemical and physical analysis on a sample.

57. The method as defined in claim 56 wherein the method further comprises the steps of:
   1) introducing ions from a sample to the cross-flow ion mobility system;
   2) detecting the ions from the sample;
   3) obtaining a measure of selected ion mobilities from the sample; and
   4) relating the measure of selected ion mobilities from the sample to a chemical identity or at least one physical property.

58. The method as defined in claim 56 wherein the method further comprises the step of detecting a wide range of chemicals selected from the group of chemicals comprised of pharmaceuticals, environmental pollutants, chemical and biological warfare agents, agrichemicals, explosives and petrochemicals.

59. The method as defined in claim 56 wherein the method further comprises the step of characterizing sizes of lipoproteins from blood samples.

60. The method as defined in claim 30 wherein the method further comprises the step of maintaining a balance as an ion travels through the gas cross-flow region so that an ion that is in balance when entering the gas cross-flow region is not rejected because the electric field changes.

61. The method as defined in claim 60 wherein the method further comprises the step of arranging the at least two electrodes so that at any given time the electric field for an ion near an exit point of the gas cross-flow region is less than for an ion near an entry point of the gas cross-flow region when scanning from low to high voltage.

62. The method as defined in claim 61 wherein the method further comprises the step of arranging the at least two electrodes so that at any given time the electric field for an ion near an exit point of the gas cross-flow region is greater than for an ion near an entry point of the gas cross-flow region when scanning from high to low voltage.

63. The method as defined in claim 62 wherein the method further comprises the step of creating a desired voltage gradient by dividing the at least two electrodes into a plurality of discrete sections.

64. The method as defined in claim 63 wherein the method further comprises the step of creating a desired voltage gradient by using non-parallel electrodes.

65. The method as defined in claim 64 wherein the method further comprises the step of making a gas cross-flow velocity lower at the exit point than at the entry point when scanning from a low to a high voltage.

66. The method as defined in claim 65 wherein the method further comprises the step of making a gas cross-flow velocity higher at the exit point than at the entry point when scanning from a high to a low voltage.

* * * * *